United States Patent [19]

Pitteloud et al.

[11] Patent Number: 4,820,756

[45] Date of Patent: Apr. 11, 1989

[54] THIOETHER SUBSTITUTED PHENOLS AND THEIR USE AS STABILIZERS

[75] Inventors: Rita Pitteloud, Fribourg; Paul Dubs, Marly, both of Switzerland

[73] Assignee: Ciba-Geigy Corporation, Ardsley, N.Y.

[21] Appl. No.: 65,226

[22] Filed: Jun. 22, 1987

[30] Foreign Application Priority Data

Jun. 26, 1986 [CH] Switzerland .................... 2589/86

[51] Int. Cl.⁴ .................... C07C 149/273; C08K 5/37; C08K 5/36
[52] U.S. Cl. .................... 524/289; 524/208; 524/326; 524/327; 524/331; 560/15; 568/47; 568/51
[58] Field of Search ............... 524/326, 327, 208, 289, 524/154, 222, 331; 560/15, 254; 562/426; 568/47, 51, 52; 558/396

[56] References Cited

U.S. PATENT DOCUMENTS

| | | | |
|---|---|---|---|
| 2,417,118 | 3/1947 | McCleary et al. | 568/51 |
| 2,668,768 | 2/1954 | Chenicek | 568/51 |
| 3,227,677 | 1/1966 | Simpson | 560/15 |
| 3,538,047 | 11/1970 | Braus et al. | 524/289 |
| 3,660,352 | 5/1972 | Song | 568/52 |
| 3,772,390 | 11/1973 | Song | 568/51 |
| 3,903,173 | 9/1975 | Eggensperger et al. | 568/51 |
| 4,020,042 | 4/1977 | Cottman | 524/289 |
| 4,021,468 | 5/1977 | Lind | 568/47 |
| 4,284,790 | 8/1981 | Hinsken et al. | 560/15 |
| 4,358,616 | 11/1982 | Wedemeyer et al. | 568/45 |
| 4,507,420 | 3/1985 | Rosenberger | 424/331 |
| 4,534,874 | 8/1985 | Steinberg et al. | 252/51.5 A |

FOREIGN PATENT DOCUMENTS

| | | |
|---|---|---|
| 035472 | 9/1981 | European Pat. Off. . |
| 0170624 | 2/1986 | European Pat. Off. . |

OTHER PUBLICATIONS

Aldrich Chemical Catalog Pages.

*Primary Examiner*—Veronica P. Hoke
*Attorney, Agent, or Firm*—Luther A. R. Hall

[57] ABSTRACT

Novel compounds of the formula I

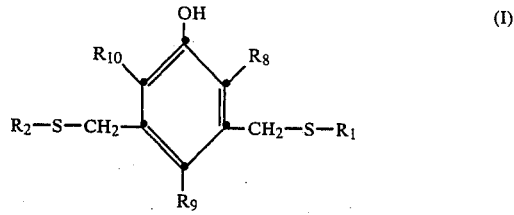

in which $R_1$, $R_2$, $R_8$, $R_9$ and $R_{10}$ are independently alkyl, alkenyl, cycloalkyl, phenyl, naphthyl, alkylphenyl or aralkyl and $R_1$ and $R_2$ may also be independently hydrogen or alkoxycarbonylmethyl, are described.

The novel phenols are suitable as stabilizers in organic polymers and lubricants.

9 Claims, No Drawings

THIOETHER SUBSTITUTED PHENOLS AND THEIR USE AS STABILIZERS

The present invention relates to novel substituted 3,5-bis-(mercaptomethyl)-phenols, a process for their preparation and their use as stabilizers for organic material.

Substituted 3,5-bis(mercaptomethyl)-phenols are known. Thus, for example, bis(alkylthiomethyl)- and bis-(arylthiomethyl)-phenols are described as intermediates for plant protection agents in German Offenlegungsschrift No. 2,838,273.

2,4,6-Trialkyl-bis(3,5-alkylthiomethyl)-phenols and 2,4,6-trialkyl-bis(3,5-alkylbenzylthiomethyl)-phenols are furthermore known as antioxidants from U.S. Pat. No. 3,660,352.

However, there is still a need for effective stabilizers for organic materials which are sensitive to degradation by heat or oxidation or induced by light.

The present invention therefore relates to compounds of the formula I

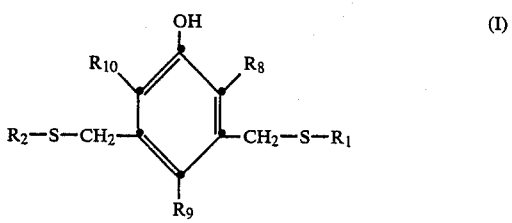

in which $R_1$ and $R_2$ independently of one another are hydrogen, $C_1$–$C_{20}$-alkyl, $C_3$–$C_{20}$-alkenyl, $C_5$–$C_{12}$-cycloalkyl, phenyl, 1-naphthyl, 2-naphthyl, $C_1$–$C_4$-alkyl-phenyl, phenyl-$C_1$–$C_4$-alkyl or a group of the formula Ia, Ib or Ic

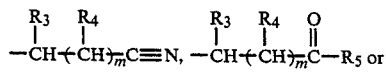

(Ia)            (Ib)

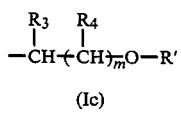

(Ic)

in which, in the case where $R_1$ and $R_2$ are simultaneously alkyl, at least one of the two substituents is a branched alkyl containing at least one tertiary C atom, or $R_1$ and $R_2$ are groups of the formula Id

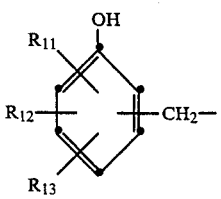

which can be identical or different, m is zero or 1, $R_3$ and $R_4$ independently of one another are hydrogen or methyl, $R_5$ is a radical $-OR_6$ or $-NR_6R_7$, R′ is hydrogen or $-CO-R_6$, $R_6$ and $R_7$ independently of one another are hydrogen, $C_1$–$C_{20}$-alkyl which may or may not be interrupted by $-O-$, $-S-$, $-NH-$, $-N(CH_3)-$ or $-N(CH_2CH_3)-$, $C_2$–$C_{20}$-alkenyl, $C_5$–$C_{12}$-cycloalkyl, phenyl, 1-naphthyl, 2-naphthyl, phenyl-$C_1$–$C_4$-alkyl or $C_1$–$C_4$-alkyl-phenyl, $R_8$, $R_9$ and $R_{10}$ independently of one another are $C_1$–$C_{10}$-alkyl, $C_2$–$C_{10}$-alkenyl, $C_5$–$C_{12}$-cycloalkyl, phenyl, 1-naphthyl, 2-naphthyl, $C_1$–$C_4$-alkyl-phenyl or phenyl-$C_1$–$C_4$-alkyl, $R_{11}$ is $C_1$–$C_{10}$-alkyl, $C_2$–$C_{10}$-alkenyl, $C_5$–$C_{12}$-cycloalkyl, $C_1$–$C_4$-alkyl-phenyl or phenyl-$C_1$–$C_4$-alkyl and $R_{12}$ and $R_{13}$ independently of one another are hydrogen or have one of the meanings of $R_{11}$.

In formula I, $R_1$ and $R_2$ are preferably other than hydrogen.

$R_1$, $R_2$, $R_6$ and $R_7$ as $C_1$–$C_{20}$-alkyl and $R_8$, $R_9$, $R_{10}$, $R_{11}$, $R_{12}$ and $R_{13}$ as $C_1$–$C_{10}$-alkyl are, for example, methyl, ethyl, n-propyl, isopropyl, n-butyl, sec.-butyl, t-butyl, n-pentyl, isopentyl, n-hexyl, 1,1-dimethylbutyl, 1,1,3,3-tetramethylbutyl, 1,1,3,3,5,5-hexamethylhexyl, n-heptyl, n-octyl, 2-ethylhexyl or n-decyl. $R_8$, $R_9$, $R_{10}$, $R_{11}$, $R_{12}$ and $R_{13}$ as alkyl are preferably $C_1$–$C_8$-alkyl, in particular $C_1$–$C_4$-alkyl.

$R_1$, $R_2$, $R_6$ and $R_7$ can moreover be, for example, 1-methylundecyl, n-dodecyl, tetradecyl, octadecyl or eicosyl. $R_1$, $R_2$, $R_6$ and $R_7$ as alkyl are preferably $C_4$–$C_{20}$-alkyl.

$R_6$ and $R_7$ as $C_1$–$C_{20}$-alkyl which may or may not be interrupted by $-O-$, $-S-$, $-N(CH_3)-$ or $-N(CH_2CH_3)-$ can be, for example, 2-methoxyethylene, 2-ethoxypropylene, 3-ethoxypropylene, 3,6-dioxaheptyl, 3,6,9-trioxaundecyl, 4-thiahexyl, 11-(methylaza)-dodecyl or 3-(ethylaza)-octadecyl. $R_6$ and $R_7$ are preferably $C_2$–$C_8$-alkyl interrupted by $-O-$.

$R_1$, $R_2$, $R_6$ and $R_7$ as $C_3$–$C_{20}$-alkenyl and $R_8$, $R_9$, $R_{10}$, $R_{11}$, $R_{12}$ and $R_{13}$ as $C_2$–$C_{10}$-alkenyl are, for example, vinyl, allyl, methallyl, penten-1-yl, 3,3-dimethylpenten-1-yl, octen-1-yl or decen-1-yl. Allyl is preferred. $R_1$, $R_2$, $R_6$ and $R_7$ can moreover be, for example, dodecen-1-yl or octadecen-1-yl.

$C_5$–$C_{12}$-cycloalkyl in the radicals $R_1$, $R_2$, $R_6$, $R_7$, $R_8$, $R_9$, $R_{10}$, $R_{11}$, $R_{12}$ and $R_{13}$ are to be understood as, for example, cycloalkyl radicals with 5–8, in particular 5 or 6, ring C atoms, which can be unsubstituted or substituted by $C_1$–$C_4$-alkyl. Examples of such radicals are cyclopentyl, methylcyclopentyl, cyclohexyl, methylcyclohexyl, ethylcyclohexyl, cycloheptyl and cyclooctyl. The unsubstituted cycloalkyl radicals may be mentioned in particular. However, cycloalkyl is preferably cyclohexyl which is unsubstituted or substituted by $C_1$–$C_4$-alkyl, in particular cyclohexyl or methylcyclohexyl, especially cyclohexyl.

Of the meanings phenyl, 1-naphthyl and 2-naphthyl for $R_1$, $R_2$, $R_6$, $R_7$, $R_8$, $R_9$ and $R_{10}$, phenyl is preferred.

$R_1$, $R_2$, $R_6$, $R_7$, $R_8$, $R_9$, $R_{10}$, $R_{11}$, $R_{12}$ and $R_{13}$ as $C_1$–$C_4$-alkyl-phenyl can be, for example, tolyl, xylyl or 4-t-butylphenyl. Phenyl here can preferably be substituted by 1 to 3 alkyl radicals.

$R_1$, $R_2$, $R_6$, $R_7$, $R_8$, $R_9$, $R_{10}$, $R_{11}$, $R_{12}$ and $R_{13}$ as phenyl-$C_1$–$C_4$-alkyl can be, for example, benzyl, α-methylbenzyl, α,α-dimethylbenzyl or α-methyl-α-ethylbenzyl. Benzyl is preferred.

Compounds which are to be mentioned in particular are those of the formula I

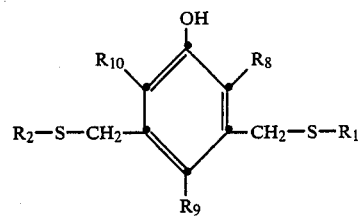

(I)

in which $R_1$ and $R_2$ independently of one another are $C_1$–$C_{20}$-alkyl, $C_3$–$C_{20}$-alkenyl, $C_5$–$C_{12}$-cycloalkyl, phenyl, 1-naphthyl, 2-naphthyl, $C_1$–$C_4$-alkyl-phenyl, phenyl-$C_1$–$C_4$-alkyl or a group of the formula Ia, Ib or Ic

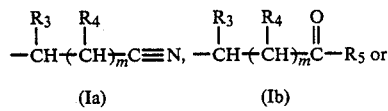

(Ia)          (Ib)

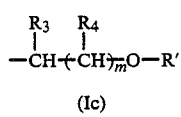

(Ic)

in which, in the case where $R_1$ and $R_2$ simultaneously are alkyl, at least one of the two substituents is branched alkyl containing at least one tertiary C atom, m is zero or 1 and R′, $R_3$, $R_4$, $R_5$, $R_6$, $R_7$, $R_8$, $R_9$ and $R_{10}$ are as defined above.

Preferred compounds of the formula I are those in which $R_1$ and $R_2$ independently of one another are a group of the formula Id, and in particular those in which $R_{11}$ and $R_{12}$ in formula Id are $C_1$–$C_{10}$-alkyl.

Compounds of the formula I which are also to be mentioned are those in which $R_1$ is $C_3$–$C_{20}$-alkenyl, $C_5$–$C_{12}$-cycloalkyl, phenyl, 1-naphthyl, 2-naphthyl, $C_1$–$C_4$-alkyl-phenyl, phenyl-$C_1$–$C_4$-alkyl or a group of the formula Ia, Ib or Ic and $R_2$ is $C_1$–$C_{20}$-alkyl or, independently of $R_1$, has one of the meanings given for $R_1$.

Compounds of the formula I which are to be singled out are furthermore those in which $R_1$ and $R_2$ have the same meaning and are hydrogen, $C_6$–$C_{20}$-alkyl with at least one tertiary C atom, a group of the formula Ib or a group of the formula Id, especially those in which, in formula Ib, $R_3$ and $R_4$ are hydrogen and $R_5$ is a radical $OR_6$, in which $R_6$ is $C_6$–$C_{18}$-alkyl, and in formula Id, $R_{11}$ is $C_1$–$C_6$-alkyl and $R_{12}$ and $R_{13}$ independently of one another are hydrogen or $C_1$–$C_6$-alkyl.

Compounds of the formula I which are of importance are those in which $R_1$ and $R_2$ have the same meaning and are $C_6$–$C_{20}$-alkyl with at least one tertiary C atom.

Compounds of the formula I which are likewise of importance are those in which $R_1$ and $R_2$ independently of one another are a group of the formula Ic.

Preferred compounds of the formula I are those in which $R_1$ is $C_5$–$C_{12}$-cycloalkyl, benzyl, phenyl or a group of the formula Ia or Ib and $R_2$ is $C_4$–$C_{20}$-alkyl or, independently of $R_1$, has one of the meanings given for $R_1$, and especially those in which $R_1$ and $R_2$ independently of one another are a group of the formula Ib.

Particularly preferred compounds of the formula I are those in which $R_1$ and $R_2$ independently of one another are a group

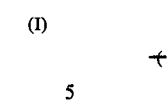

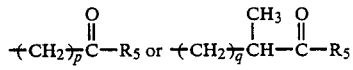

in which p is the number 1 or 2, q is zero or 1 $R_5$ is as defined above, in particular those in which $R_5$ is —$OR_6$ or —$NR_6R_7$, $R_6$ is $C_1$–$C_{18}$-alkyl which may or may not be interrupted by —O—, $C_5$–$C_{12}$-cycloalkyl, phenyl, 1-naphthyl, 2-naphthyl, phenyl-$C_1$–$C_4$-alkyl or $C_1$–$C_4$-alkylphenyl, $R_7$ independently of $R_6$ has one of the meanings given for $R_6$ and $R_8$, $R_9$ and $R_{10}$ independently of one another are $C_1$–$C_8$-alkyl, $C_5$–$C_{12}$-cycloalkyl, phenyl or benzyl. Preferably, $R_8$, $R_9$ and $R_{10}$ are $C_1$–$C_8$-alkyl, in particular $C_1$–$C_4$-alkyl, and they preferably have the same meaning.

In particularly preferred compounds of the formula I, $R_1$ and $R_2$ are identical.

Compounds of the formula I which should also be mentioned are those in which $R_1$ and $R_2$ are identical and are each a group of the formula Id. The OH group is preferably in the meta-position relative to the —$CH_2$—S— linkage.

Compounds of the formula I in which $R_1$ and $R_2$ are —$CH_2$—COO—$CH_2$—$CH(CH_2CH_3)$—$(CH_2)_3$—$CH_3$ and $R_8$, $R_9$ and $R_{10}$ are methyl are of particular interest.

Compounds of the formula I in which $R_1$ and $R_2$ are hydrogen are also of particular interest.

Examples which may be mentioned of representatives of the compounds of the formula I according to the invention are: 3,5-bis(mercaptomethyl)-2,4,6-trimethyl-phenol, 3,5-bis(2′-hydroxyethylthiomethyl)-2,4,6-trimethyl-phenol, 3,5-bis(3′-methylamido-propyl-thiomethyl)-2,4,6-trimethyl-phenol, 3,5-bis(3′-dimethylamido-propylthiomethyl)-2,4,6-trimethyl-phenol, 3,5-bis(1′-cyanoethylidenethiomethyl)-2,4,6-trimethyl-phenol, 3,5-bis(4′-n-decanoyloxybutyl-thiomethyl)-2,4,6-trimethyl-phenol, 3-(t-octylthiomethyl)-5-(benzyl-thiomethyl)-2,4,6-trimethyl-phenol,[1], 3-(t-dodecylthiomethyl)-5-(2′-acetoxyethyl-thiomethyl)-2,4,6-trimethyl-phenol,[2], 3,5-bis(benzylthiomethyl)-2,4,6-trimethyl-phenol, 3,5-bis(phenylthiomethyl)-2,6-dimethyl-4-t-butyl-phenol, 3,5-bis(naphth-1-yl-thiomethyl)-2,4,6-trimethyl-phenol, 3,5-bis(2′-ethoxy-carbonylmethyl-thiomethyl)-2,4,6-trimethyl-phenol, 3,5-bis(n-octadecyloxycarbonylmethyl-thiomethyl)-2,4,6-trimethyl-phenol and 3,5-bis[(3′-methyl-4′-hydroxy-5′-t-butyl)benzyl-thiomethyl]-2,4,6-trimethylphenol.

[1] t-octyl is 1,1,3,3-tetramethylbutyl
[2] t-dodecyl is a mixture of 1,1,3,3,5,5-hexamethylhexyl and 1,1,4,6,6-pentamethylhept-4-yl The preparation, which is known per se, of the compounds of the formula I according to the invention is carried out, for example, by reacting a compound of the formula II

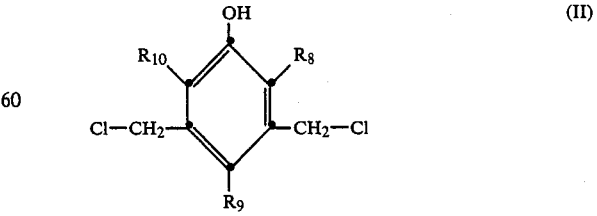

(II)

with a mercaptan $R_1$—SH or with a mixture of $R_1$—SH/$R_2$—SH in the presence of a base, $R_1$, $R_2$, $R_8$, $R_9$ and $R_{10}$ being as defined above.

In the case of $R_1$—SH/$R_2$—SH mixtures, the mixing ratio is preferably 1:1.

Suitable bases are organic and inorganic bases. Examples of suitable organic bases are tertiary amines, for example triethylamine, pyridine or N,N-dimethylaniline, or alcoholates, for example sodium ethylate. Suitable inorganic bases in solid or liquid form are, for example, carbonates, for example sodium bicarbonate or potassium carbonate, or alkali metal and alkaline earth metal hydroxides, for example sodium hydroxide or potassium hydroxide.

The reaction can advantageously be carried out in the temperature range from −20° C. to 160° C. The temperature range from 0° C. to 80° C. is preferred.

The reaction can advantageously be carried out under an $N_2$ atmosphere in the stated temperature range for 0.5 to 3 hours, the temperature being chosen so that the reaction mixture is heated under reflux.

The compounds of the formula I according to the invention can also be obtained, for example, by reacting a compound of the formula

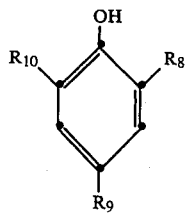

with a compound $R_1$—X or with a mixture of $R_1$—S—$CH_2$—X/$R_2$—S—$CH_2$—X in the presence of a catalyst, $R_1$, $R_2$, $R_8$, $R_9$ and $R_{10}$ being as defined above. X is halogen, tosyl, mesyl, OH, alkoxy or acyloxy, for example acetoxy.

Suitable catalysts are Bronstedt or Lewis acids, for example $ZnCl_2$ or $SnCl_4$.

The compounds of the formula I according to the invention in which $R_1=R_2=H$

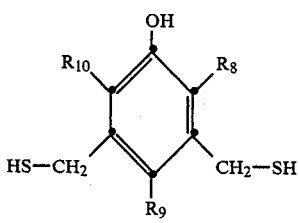

(I)

can be prepared, for example, by reacting a compound of the formula II with thiourea. The symbols $R_8$, $R_9$ and $R_{10}$ are as defined above.

The reaction can advantageously be carried out in the presence of a suitable solvent, for example an ether, under an $N_2$ atmosphere in a temperature range from 80° to 250° C. for 0.5 to 6 hours, the temperature being chosen so that the reaction mixture boils under reflux.

The compounds of the formula I according to the invention in which $R_1$ and $R_2$ independently of one another are a group of the formula Id

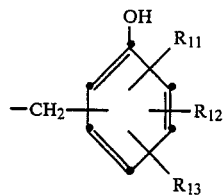

(Id)

and $R_{11}$, $R_{12}$ and $R_{13}$ are as defined above, can be prepared, for example, by reacting a compound according to the invention, of the formula

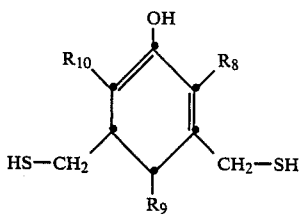

with a phenolic Mannich base of the formula

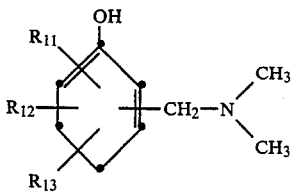

or mixtures thereof. The symbols $R_8$, $R_9$ and $R_{10}$ are as defined above.

The reaction can advantageously be carried out in the temperature range from 80° C. to 250° C., preferably from 100° C. to 180° C., under an $N_2$ atmosphere for 0.5 to 5 hours.

The compounds of the formula I according to the invention in which $R_1$ and $R_2$ independently of one another are groups of the formula Id can also be obtained, for example, by reacting a compound according to the invention, of the formula

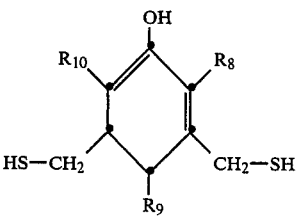

with a compound of the formula

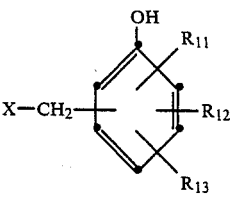

in the presence of a base.

X represents a leaving group, for example halogen, acetate, tosylate or mesylate, and the symbols $R_8$, $R_9$, $R_{10}$, $R_{11}$, $R_{12}$ and $R_{13}$ are as defined above.

The suitable bases and advantageous conditions for the reaction have been described previously.

The reactions can be carried out in the presence of a solvent. Suitable solvents are aliphatic, cycloaliphatic or aromatic hydrocarbons, for example hexane, cyclohexane or toluene, halogenated hydrocarbons, for example methylene chloride or chloroform, alcohols, ethers and polar aprotic solvents, for example dimethylformamide. Mixtures of the solvents mentioned can also be used.

The compounds of the formula I according to the invention are advantageously separated off from any hydrochlorides or other solid residues obtained by a suitable method, for example filtration and/or washing with aqueous hydrochloric acid, and are isolated by distilling off or evaporating off the solvent (if appropriate under reduced pressure). They can be further purified by suitable purification methods, for example recrystallization or column chromatography.

If the reaction is carried out with mixtures of mercaptans $R_1$—SH/$R_2$—SH, as a rule random mixtures of symmetrically and unsymmetrically substituted end products of the formula I are obtained. These can be separated into the individual components by customary separation methods (for example by those described in the above paragraph). However, they can also be used directly as stabilizers in the form of the mixtures.

The starting substances of the formula II, the phenolic Mannich bases and the mercaptans $R_1$—SH and $R_2$—SH are known compounds and can be prepared by known processes. Some of them are also commercially available.

The compounds according to the invention are effective stabilizers for organic materials which are sensitive to degradation by heat and oxidation or induced by radiation.

The invention therefore also relates to the use of the compounds of the formula I according to the invention as stabilizers against degradation by heat or oxidation or induced by radiation in an organic material.

The use of the compounds of the formula I according to the invention as antioxidants in synthetic polymers, for example thermoplastics or elastomers, or their use in lubricants, for example in mineral oils or synthetic oils, is preferred.

Their use in polyolefines, for example in polypropylene, is particularly preferred.

Examples of organic materials which can advantageously be stabilized by the compounds of the formula I according to the invention are:

1. Polymers of mono- and diolefines, for example polyethylene (which can be non-crosslinked or crosslinked), polypropylene, polyisobutylene, polybut-1-ene, polymethylpent-1-ene, polyisoprene or polybutadiene, and polymers of cycloolefines, for example of cyclopentene or norbornene.

2. Mixtures of the polymers mentioned under (1), for example mixtures of polypropylene with polyisobutylene.

3. Copolymers of mono- and diolefines with one another or with other vinyl monomers, for example ethylene-propylene copolymers, propylene-but-1-ene copolymers, propylene-isobutylene copolymers, ethylene-but-1-ene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers and salts thereof (ionomers), as well as terpolymers of ethylene with propylene and a diene, such as hexadiene, dicyclopentadiene or ethylidenenorbornene.

4. Polystyrene and poly-(p-methylstyrene).

5. Copolymers of styrene or α-methylstyrene with dienes or acrylic derivatives, for example styrene-butadiene, styrene-acrylonitrile, styrene-alkyl methacrylate, styrenemaleic anhydride and styrene-acrylonitrile-methyl acrylate; high impact strength mixtures of styrene copolymers and another polymer, for example a polyacrylate, a diene polymer or an ethylene-propylene-diene terpolymer; and block copolymers of styrene, for example styrene-butadiene-styrene, styrene-isoprene-styrene, styrene-ethylene/butylene-styrene or styrene-ethylene/propylene-styrene.

6. Graft copolymers of styrene, for example styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers and mixtures thereof with the copolymers mentioned under (5), such as are known, for example, as so-called ABS, MBS, ASA or AES polymers.

7. Halogen-containing polymers, for example polychloroprene, chlorinated rubber, chlorinated or chlorosulfonated polyethylene and epichlorohydrin homo- and copolymers, in particular polymers of halogen-containing vinyl compounds, for example polyvinyl chloride, polyvinylidene chloride, polyvinyl fluoride and polyvinylidene fluoride; and copolymers thereof, such as vinyl chloride-vinylidene chloride, vinyl chloride-vinyl acetate or vinylidene chloride-vinyl acetate.

8. Polymers which are derived from αβ-unsaturated acids and derivatives thereof, such as polyacrylates and polymethacrylates, polyacrylamides and polyacrylonitriles.

9. Copolymers of the monomers mentioned under (8) with one another or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

10. Polymers which are derived from unsaturated alcohols and amines or their acyl derivatives or acetals, such as polyvinyl alcohol, polyvinyl acetate, stearate, benzoate or maleate, polyvinylbutyral, polyallyl phthalate and polyallylmelamine.

11. Homo- and copolymers of cyclic ethers, such as polyalkylene glycols, polyethylene oxide, polypropylene oxide or copolymers thereof with bisglycidyl ethers.

12. Polyacetals, such as polyoxymethylene, and those polyoxymethylenes which contain comonomers, for example ethylene oxide.

13. Polyphenyl oxides and sulfides and mixtures thereof with styrene polymers.

14. Polyurethanes which are derived from polyethers, polyesters and polybutadienes with terminal hydroxyl groups on the one hand and aliphatic or aromatic polyisocyanates on the other hand, and precursors thereof.

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-m-phenylene-isophthalamide, and block copolymers thereof with polyethers, for example with polyethylene glycol, polypropylene glycol or polytetramethylene glycol.

16. Polyureas, polyimides, polyamide-imides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, as well as block polyether-esters which are derived from polyethers with hydroxyl end groups.

18. Polycarbonates and polyester-carbonates.

19. Polysulfones, polyether-sulfones and polyether-ketones.

20. Crosslinked polymers which are derived from aldehydes on the one hand and phenols, urea or melamine on the other hand, such as phenol-formaldehyde, urea-formaldehyde and melamine-formaldehyde resins.

21. Drying and non-drying alkyd resins.

22. Unsaturated polyester resins which are derived from copolyesters of saturated and unsaturated dicarboxylic acids with polyhydric alcohols, and vinyl compounds as crosslinking agents, as well as their halogen-containing modifications of low flammability.

23. Crosslinkable acrylic resins which are derived from substituted acrylic acid esters, for example from epoxyacrylates, urethane-acrylates or polyester-acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bis-glycidyl ethers or cycloaliphatic diepoxides.

26. Naturally occurring polymers, such as cellulose, natural rubber, gelatine and polymer-homologous chemically modified derivatives thereof, such as cellulose acetates, propionates and butyrates, and the cellulose ethers, such as methylcellulose.

27. Mixtures (polyblends) of the abovementioned polymers, for example PP/EPDM, polyamide 6/EPDM or ABS, PVC/EVA, PVC/ABS, PVC/MBS, PC/ABS and PBTP/ABS.

28. Naturally occurring and synthetic organic substances which are pure monomeric compounds or mixtures of these, for example mineral oils, animal and vegetable fats, oils and waxes or oils, waxes and fats based on synthetic esters (for example phthalates, adipates, phosphates or trimellitates), and mixtures of synthetic esters with mineral oils in any desired weight ratios, such as are used, for example, as spinning preparations, and aqueous emulsions thereof.

29. Aqueous emulsions of natural or synthetic rubbers, for example natural rubber latex or latices of carboxylated styrene-butadiene copolymers.

The lubricants in question are familiar to the expert and are described, for example, in "Schmiermittel Taschenbuch" ("Lubricants Pocketbook") (Hüthig Verlag, Heidelberg, 1974).

The stabilizers according to the invention are advantageously added to the polymers or lubricants in a concentration of 0.01–10% by weight, calculated on the material to be stabilized. Preferably, 0.05 to 5.0% by weight, especially preferably 0.1 to 2.0% by weight, of the compounds of the formula I, calculated on the material to be stabilized, are incorporated into this material.

The incorporation can be effected, for example, by mixing in the stabilizers according to the invention and if appropriate other additives by methods customary in the art before or during shaping, or by application of the dissolved or dispersed compounds onto the polymer, if appropriate with subsequent evaporation of the solvent. The stabilizers according to the invention can also be added in the form of a masterbatch, which contains the stabilizer in a concentration of, for example, 2.5 to 25% by weight, to the plastics to be stabilized.

The compounds of the formula I can also be added before or during the polymerization or the crosslinking reaction. Directly stabilized polymers are thus obtained.

The materials thus stabilized can be used in widely different forms, for example as films, fibres, tapes, moulding compositions or profiles, or as binders for lacquers, adhesives or cement.

The present invention also relates to compositions containing an organic material which is sensitive to degradation by heat or oxidation or induced by radiation and, as a stabilizer, at least one compound of the formula I. Examples of such organic materials are listed above.

Compositions in which the organic material is a synthetic polymer are preferred.

The polymers can also be in the form of latices, and can be stabilized as such.

The polymer is preferably a thermoplastic or an elastomer, in particular a polyolefin, for example polypropylene.

Compositions in which the organic material is a lubricant, in particular a synthetic lubricant or a lubricant based on mineral oil, are also preferred.

In practice, the compounds of the formula I according to the invention can also be used as mixtures (as already described above) or/and together with other stabilizers.

The compositions can additionally also contain other additives, which are added to improve certain use properties, for example amine antioxidants, metal passivators, rust inhibitors, agents which improve the viscosity index, agents which reduce the pour point, dispersing agents/surfactants and wear protection additives.

Examples which may be mentioned of other additives with which the stabilizers used according to the invention can be employed together are:

1. Antioxidants 1.1. Alkylated monophenols, for example 2,6-di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-di-cyclopentyl-4-methylphenol, 2-($\alpha$-methylcyclohexyl)-4,6-dimethylphenol, 2,6-di-octadecyl-4-methylphenol, 2,4,6-tricyclohexylphenol and 2,6-di-tert.-butyl-4-methoxymethylphenol.

1.2. Alkylated hydroquinones, for example 2,6-di-tert.-butyl-4-methoxyphenyl, 2,5-di-tert.-butyl-hydroquinone, 2,5-di-tert.-amyl-hydroquinone and 2,6-diphenyl-4-octadecyloxyphenol.

1.3. Hydroxylated diphenyl thioethers, for example 2,2'-thio-bis-(6-tert.-butyl-4-methylphenol), 2,2'-thio-bis-(4-octylphenol), 4,4'-thio-bis-(6-tert.-butyl-3- methylphenol) and 4,4'-thio-bis-(6-tert.-butyl-2-methylphenol).

1.4. Alkylidene-bisphenols, for example 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-tert.-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)-butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], di-(3-tert.-butyl-4-hydroxy-5-methylphenyl)-dicyclopentadiene and di-[2-(3'-tert.-butyl-2'-hydroxy-5'-methyl-benzyl)-6-tert.-butyl-4-methyl-phenyl]terephthalate.

1.5. Benzyl compounds, for example 1,3,5-tri-(3,5-di-tert.-butyl-4-hydroxybenzyl)-2,4,6-trimethylbenzene, di-(3,5-di-tert.-butyl-4-hydroxybenzyl)sulfide, isooctyl 3,5-di-tert.-butyl-4-hydroxybenzyl-mercaptoacetate, bis-(4-tert.-butyl-3-hydroxy-2,6-dimethylbenzyl)dithiol terephthalate, 1,3,5-tris-(3,5-di-tert.-butyl-4-hydroxybenzyl)isocyanurate, 1,3,5-tris-(4-tert.-butyl-3-hydroxy-2,6-dimethylbenzyl)isocyanurate, dioctadecyl 3,5-di-tert.-butyl-4-hydroxybenzyl-phosphonate and the calcium salt of monoethyl 3,5-di-tert.-butyl-4-hydroxybenzyl-phosphonate.

1.6. Acylaminophenols, for example 4-hydroxy-lauric acid anilide, 4-hydroxy-stearic acid anilide, 2,4-bis-octylmercapto-6-(3,5-di-tert.-butyl-4-hydroxyanilino)-s-triazine and octyl N-(3,5-di-tert.-butyl-4-hydroxy-phenyl)-carbamate.

1.7. Esters of β-(3,5-di-tert.-butyl-4-hydroxyphenyl)-propionic acid with mono- or polyhydric alcohols, for example with methanol, octadecanol, 1,6-hexanediol, neopentylglycol, diethylene thioglycol, diethylene glycol, triethylene glycol, pentaerythritol, tris-hydroxyethyl isocyanurate and dihydroxyethyl-oxalic acid diamide.

1.8. Esters of β-(5-tert.-butyl-4-hydroxy-3-methylphenyl)-propionic acid with mono- or polyhydric alcohols, for example with methanol, octadecanol, 1,6-hexanediol, neopentylglycol, diethylene thioglycol, diethylene glycol, triethylene glycol, pentaerythritol, tris-hydroxyethyl isocyanurate and dihydroxyethyl-oxalic acid diamide.

1.9. Amides of β-(3,5-di-tert.-butyl-4-hydroxyphenyl)-propionic acid, for example N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)-hydrazine.

1.10. Amine antioxidants, for example N,N'-di-isopropyl-p-phenylenediamine, N,N'-di-sec.-butyl-p-phenylenediamine, N,N'-bis(1,4-dimethyl-pentyl)-p-phenylenediamine, N,N'-bis-(1-ethyl-3-methyl-pentyl)-p-phenylenediamine, N,N'-bis(1-methyl-heptyl)-p-phenylenediamine, N,N'-diphenyl-p-phenylenediamine, N,N'-di-(naphth-2-yl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec.-butyl-p-phenylenediamine, diphenylamine, 4-isopropoxy-diphenylamine, N-phenyl-1-naphthylamine, N-phenyl-2-naphthylamine, octylated diphenylamine, 4-n-butylaminophenol, 4-butyrylamino-phenol, 4-nonanoylamino-phenol, 4-dodecanoylamino-phenol, 4-octadecanoylamino-phenol, di-(4-methoxyphenyl)-amine, 2,6-di-tert.-butyl-4-dimethylaminomethyl-phenol, 2,4'-diamino-diphenylmethane, 4,4'-diaminodiphenylmethane, N,N,N',N'-tetramethyl-4,4'-diaminodiphenylmethane, 1,2-di-[(2-methyl-phenyl)-amino]-ethane, 1,2di-(phenylamino)-propane, (o-tolyl)-biguanide and di-[4-(1',3'-dimethyl-butyl)-phenyl]amine.

2. UV absorbers and light stabilizers 2.1. 2-(2'-Hydroxyphenyl)-benzotriazoles, for example the 5'-methyl, 3',5'-di-tert.-butyl, 5'-tert.-butyl, 5'-(1,1,3,3-tetramethylbutyl), 5-chloro-3', 5'-di-tert.-butyl, 5-chloro-3'-tert.-butyl-5'-methyl, 3'-sec.-butyl-5'-tert.-butyl, 4'-octoxy, 3',5'-di-tert.-amyl and 3',5'-bis-(α,α-dimethyl-benzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert.-butyl-phenyl salicylate, phenyl salicylate, octylphenyl salicylate, dibenzoyl-resorcinol, bis-(4tert.-butylbenzoyl)-resorcinol, benzoylresorcinol, 2,4-di-tert.-butylphenyl, 3,5-di-tert.-butyl-4-hydroxybenzoate and hexadecyl 3,5-di-tert.-butyl-4-hydroxybenzoate.

2.4. Acrylates, for example ethyl and isooctyl α-cyano-β,β-diphenylacrylate, methyl α-carbomethoxy-cinnamate, methyl and butyl α-cyano-β-methyl-p-methoxy-cinnamate, methyl α-carbomethoxy-p-methoxy-cinnamate and N-(β-carbomethoxy-β-cyanovinyl)-2-methyl-indoline.

2.5. Nickel compounds, for example nickel complexes of 2,2'-thio-bis-[4-(1,1,3,3-tetramethylbutyl)-phenol], such as the 1:1 or 1:2 complex, with or without additional ligands, such as n-butylamine, triethanolamine or N-cyclohexyl-diethanolamine, nickel dibutyl-dithiocarbamate, nickel salts of monoalkyl 4-hydroxy-3,5-di-tert.-butylbenzyl-phosphonates, such as the methyl or ethyl ester, nickel complexes of ketoximes, such as 2-hydroxy-4-methyl-phenyl-undecylketone oxime, and nickel complexes of 1-phenyl-4-lauroyl-5-hydroxypyrazole, with or without additional ligands.

2.6. Sterically hindered amines, for example bis-(2,2,6,6-tetramethylpiperidyl)sebacate, bis-(1,2,2,6,6-pentamethylpiperidyl) sebacate, bis(1,2,2,6,6-pentamethylpiperidyl)n-butyl-3,5-di-tert.-butyl-4-hydroxybenzyl-malonate, the condensation product of 1-hydroxyethyl-2,2,6,6-tetramethyl-4-hydroxypiperidine and succinic acid, the condensation product of N,N'-(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl)nitrilotriacetate, tetrakis-(2,2,6,6-tetramethyl-4-piperidyl)-1,2,3,4-butanetetracarboxylic acid and 1,1'-(1,2-ethanediyl)-bis-(3,3,5,5-tetramethyl-piperazinone).

2.7. Oxalic acid diamides, for example 4,4'-di-octyloxyoxanilide, 2,2'-dioctyloxy-5,5'-di-tert.-butyl-oxanilide, 2,2'-di-dodecyloxy-5,5'-di-tert.-butyl-oxanilide, 2- ethoxy-2'-ethyl-oxanilide, N,N'-bis-(3-dimethylaminopropyl)-oxalamide, 2-ethoxy-5-tert.-butyl-2'-ethyloxanilide and its mixture with 2-ethoxy-2'-ethyl-5,4'-di-tert.-butyl-oxanilide, and mixtures of o- and p-methoxy- and of o- and p-ethoxy-disubstituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole and bis-benzylidene-oxalic acid dihydrazide.

4. Phosphites and phosphonites, for example triphenyl phosphite, diphenyl alkyl phosphites, phenyl dialkyl phosphites, tri-(nonylphenyl)phosphite, trilauryl phosphite, trioctadecyl phosphite, distearyl-pentaerythritol diphosphite, tris(2,4-di-tert.-butylphenyl)-phosphite, diisodecylpentaerythritol diphosphite, di-(2,4-di-tert.-butylphenyl)-pentaerythritol diphosphite, tristearyl-sorbitol triphosphite, tetrakis-(2,4-di-tert.-butylphenyl)-4,4'-biphenylene diphosphonite and 3,9-bis-(2,4-di-tert.-butylphenoxy-2,4,8,10-tetraoxa-3,9-diphosphaspiro[5.5]undecane.

5. Compounds which destroy peroxide, for example esters of β-thio-dipropionic acid, for example the lauryl, stearyl, myristyl or tridecyl ester, mercaptobenzimidazole, the zinc salt of 2-mercaptobenzimidazole, zinc dibutyl-dithiocarbamate, dioctadecyl disulfide and pentaerythritol tetrakis-(β-dodecylmercapto)-propionate.

6. Polyamide stabilizers, for example copper salts in combination with iodides and/or phosphorus compounds and salts of divalent manganese.

7. Basic costabilizers, for example melamine, polyvinyl-pyrrolidone, dicyandiamide, triallyl cyanurate, urea derivatives, hydrazine derivatives, amines, polyamides, polyurethanes and alkali metal and alkaline earth metal salts of higher fatty acids, for example Ca stearate, Zn stearate, Mg stearate, Na ricinoleate, K palmitate, antimony pyrocatecholate or tin pyrocatecholate.

8. Nucleating agents, for example 4-tert.-butylbenzoic acid, adipic acid and diphenylacetic acid.

9. Fillers and reinforcing agents, for example calcium carbonate, silicates, glass fibres, asbestos, talc, kaolin, mica, barium sulfate, metal oxides and hydroxides, carbon black and graphite.

10. Other additives, for example plasticizers, lubricants, emulsifiers, pigments, optical brighteners, flameproofing agents, antistatics and blowing agents.

11. Metal passivators for copper, for example: triazole, benzotriazole and derivatives thereof, 2-mercaptobenzothiazole, 2,5-dimercaptothiadiazole, salicylidene-propylenediamine and salts of salicylaminoguanidine.

12. Rust inhibitors:

(a) Organic acids and their esters, metal salts and anhydrides, for example: N-oleoyl-sarcosine, sorbitan monooleate, lead naphthenate, dodecenylsuccinic acid anhydride, alkenyl-succinic acid half-ester and 4-nonylphenoxy-acetic acid.

(b) Nitrogen-containing compounds, for example: I. Primary, secondary or tertiary aliphatic or cycloaliphatic amines and amine salts of organic and inorganic acids, for example oil-soluble alkylammonium carboxylates, II. Heterocyclic compounds, for example: substituted imidazolines and oxazolines.

(c) Phosphorus-containing compounds, for example: amine salts of phosphoric acid partial esters.

(d) Sulfur-containing compounds, for example: barium dinonylnaphthalene-sulfonates and potassium petroleum-sulfonates.

13. Agents which improve the viscosity index: Polymethacrylates, vinylpyrrolidone/methacrylate copolymers, polybutenes, olefine copolymers, styrene/acrylate copolymers.

14. Agents which reduce the pour point: Polymethacrylate and alkylated naphthalene derivatives.

15. Dispersing agents/surfactants: Polybutenylsuccinic acid imides, polybutenylphosphonic acid derivatives and basic magnesium, calcium and barium sulfonates and phenolates.

16. Wear protection additives: Compounds containing sulfur and/or phosphorus and/or halogen, such as sulfurized vegetable oils, zinc dialkyldithiophosphates, tritolyl phosphate, chlorinated paraffins and alkyl and aryl disulfides.

Compositions which contain at least one compound of the formula I together with at least one S-containing additive as a stabilizer are of particular interest.

The following examples illustrate the invention in more detail. Percentages and parts in the examples, the rest of the description and the patent claims are percentages by weight and parts by weight.

PREPARATION EXAMPLES

Example 1

3,5-Bis(2'-ethylhexyloxycarbonylmethyl-thiomethyl)-2,4,6-trimethyl-phenol $$CH_3{\text-}(CH_2)_3{\text-}CH(CH_2CH_3){\text-}CH_2{\text-}OOC{\text-}CH_2{\text-}S{\text-}CH_2{\text-}[2,4,6\text{-trimethyl-3,5-disubstituted phenol}]{\text-}CH_2{\text-}S{\text-}CH_2{\text-}COO{\text-}CH_2{\text-}CH(CH_2CH_3){\text-}(CH_2)_3CH_3$$

9 ml of triethylamine are added dropwise to a mixture of 5 g of 3,5-bis(chloromethyl)-mesitol, 9.5 ml of 2-ethylhexyl 2-mercapto-acetate and 40 ml of ethanol at room temperature under nitrogen. The reaction mixture is stirred at room temperature for two hours and then poured onto 1N hydrochloric acid and extracted with ether.

After the ether phase has been evaporated on a rotary evaporator, 3,5-bis(2'-ethylhexyloxycarbonylmethyl-thiomethyl)-2,4,6-trimethyl-phenyl is obtained as a white powder (melting point 58°–59° C.) in a yield of 93% of theory.

Analysis: calculated: S 11.27%; found: S 11.27%.

Example 2

3,5-Bis(t-dodecylthiomethyl)-2,4,6-trimethylphenol.

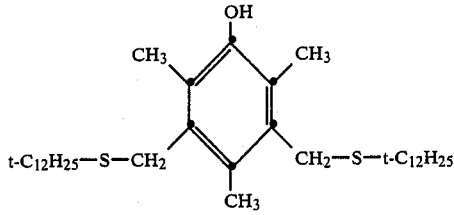

10.7 ml of 1,8-diazabicyclo(5,4,0)undec-7-ene are added dropwise to a mixture of 8 g of 3,5-bis(chloromethyl)-mesitol, 14.6 g of t-dodecylmercaptan and 80 ml of acetonitrile at room temperature under nitrogen.

The mixture is stirred at room temperature for two hours. The solvent is then distilled off and the residue is taken up in hexane/ether 1:1. The salts are filtered off and the organic phase is washed first with 1N hydrochloric acid and then with water. Evaporation on a rotary evaporator gives 17 g of 3,5-bis(t-dodecylthiomethyl)-2,4,6-trimethylphenol as a colourless oil, which can be further purified by column chromatography.

Example 3

3,5-Bis(mercaptomethyl)-2,4,6-trimethyl-phenol

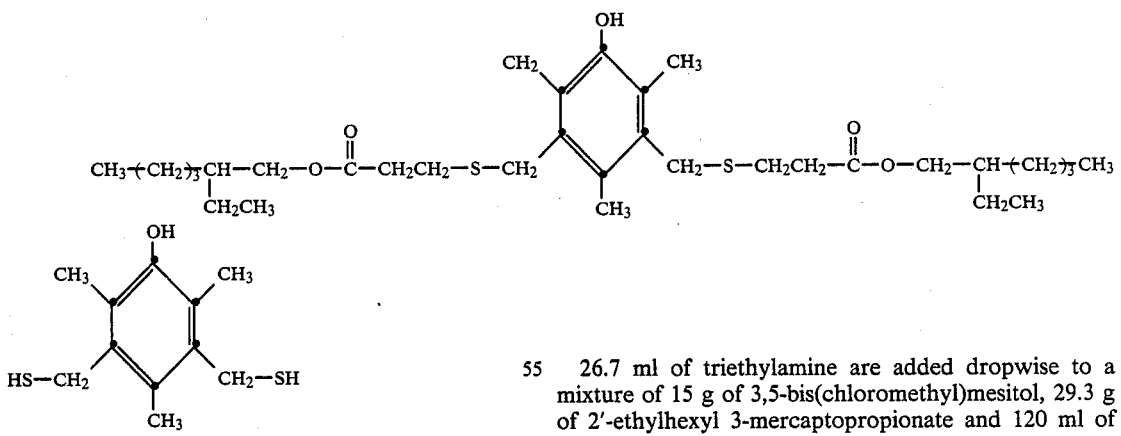

A solution of 60 g of 3,5-bis(chloromethyl)-2,4,6-trimethyl-phenol in 500 ml of diethylene glycol monomethyl ether is added dropwise to a solution of 42.8 g of thiourea in 360 ml of diethylene glycol monomethyl ether at 125° C. under nitrogen. The mixture is refluxed for 5 hours and the solvent is then evaporated off on a rotary evaporator.

The solid residue is taken up in 500 ml of 2N NaOH and the mixture is refluxed for 2 hours. The resulting mixture is then poured onto 2N HCl. The product which has precipitated is filtered off, washed neutral with water and finally dried at 95° C. in vacuo.

56 g (96% of theory) of 3,5-bis(mercaptomethyl)-2,4,6-trimethyl-phenol are obtained as a white powder, which can be purified still further by recrystallization (melting point 159° C.).

Analysis: calculated: S 28.08%; found: S 28.09%.

Example 5

3,5-Bis(n-octadecyloxycarbonylethyl-thiomethyl)-2,4,6-trimethyl-phenol

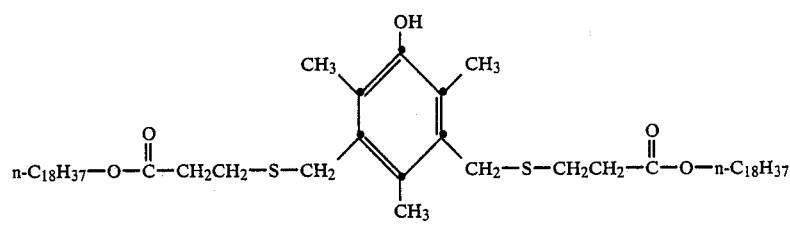

14.5 ml of triethylamine are added dropwise to a mixture of 8 g of 3,5-bis(chloromethyl)-mesitol, 26 g of n-octadecyl 3-mercaptopropionate, 0.43 g of dimethylaminopyridine and 120 ml of an acetonitrile/chloroform mixture (1:1) at 10° C. under nitrogen.

The mixture is stirred at room temperature for 15 hours. The solvent is then distilled off, the residue is taken up in toluene and the insoluble salts are filtered off. After the toluene phase has been evaporated, 30 g of 3,5-bis(n-octadecyloxycarbonylethyl-thiomethyl)-2,4,6-trimethyl-phenol are obtained as a white powder which can be further purified by recrystallization (melting point 66°-70° C.).

Analysis: calculated: S 7.31%; found: S 7.49%.

Example 5

3,5-Bis(2'-ethylhexyloxycarbonylethyl-thiomethyl)-2,4,6-trimethyl-phenol 26.7 ml of triethylamine are added dropwise to a mixture of 15 g of 3,5-bis(chloromethyl)mesitol, 29.3 g of 2'-ethylhexyl 3-mercaptopropionate and 120 ml of acetonitrile at 0° C. under nitrogen.

The reaction mixture is stirred at room temperature for two hours. Working up as under Example 2, followed by column chromatography, gives 32.5 g of 3,5-bis(2'-ethylhexyloxycarbonylethyl-thiomethyl)-2,4,6-trimethyl-phenol as a white powder (melting point 30°-32° C.).

Analysis: calculated: S 10.74%; found: S 10.72%.

Example 6

3,5-Bis(t-octylthiomethyl)-2,4,6-trimethyl-phenol

Example 8

3,5-Bis[(3'-t-butyl-4'-hydroxy-5'-methyl)benzylthiomethyl]-2,4,6-trimethyl-phenol

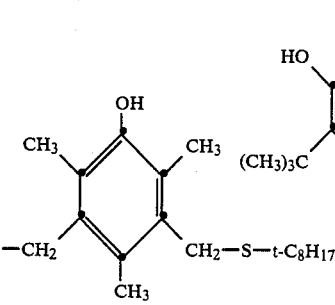

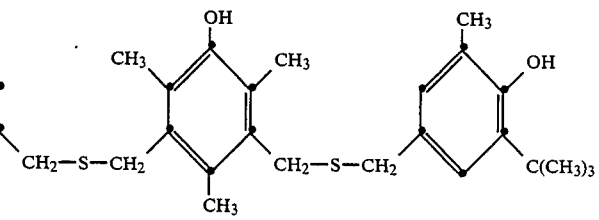

21.1 ml of 1,8-diazabicyclo(5,4,0)undec-7-ene are added dropwise to a mixture of 15 g of 3,5-bis(chloromethyl)-mesitol, 20.7 g of t-octylmercaptan and 120 ml of acetonitrile at 0° C. under nitrogen. The mixture is stirred at room temperature for 15 minutes.

After working up as under Example 2, 28 g of 3,5-bis(t-octylthiomethyl)-2,4,6-trimethyl-phenol are obtained as a white powder which can be further purified by recrystallization (melting point 98°–101° C.).

Analysis: calculated: S 14.16%; found: S 14.24%.

Example 7

3,5-Bis(2'-ethylhexyloxycarbonylmethyl-thiomethyl)-2,4-dimethyl-6-ethylphenol 2,4-dimethyl-6-ethylphenol are obtained as a pale yellow oil.

Analysis: calculated: S 11.0%; found: S 10.89%.

A mixture of 6 g of 3,5-bis(mercaptomethyl)-2,4,6-trimethyl-phenol, 12.8 g of 2-t-butyl-4-(N,N-dimethylaminomethyl)-6-methylphenol and 150 ml of dimethylformamide is heated at 100° C. under 200 mm Hg for 2 hours. After cooling, the reaction mixture is poured onto 1N hydrochloric acid and extracted with ethyl acetate.

After evaporation of the solvent and purification of the residue by column chromatography, 12.5 g of the product are obtained as a powder (melting point 82° C.).

Analysis: calculated: S 11.04%; found: S 10.77%.

Example 9

3,5-Bis[(2'6'-dimethyl-4'-t-butyl-3'-hydroxy)-benzylthiomethyl]-2,4,6-trimethyl-phenol

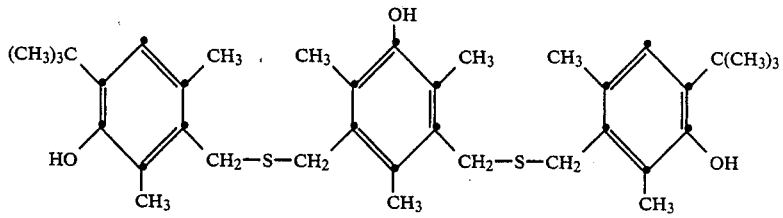

11.3 ml of triethylamine are added dropwise to a mixture of 5 g of 3,5-bis(mercaptomethyl)-2,4,6-trimethyl-phenol, 12.9 g of 6-t-butyl-3-chloromethyl-2,4-dimethylphenol and 100 ml of methylene chloride at 0° C. under a nitrogen atmosphere. The mixture is then refluxed for 15 hours. Working up as under Example 1, followed by column chromatography, gives 9 g of the product as a powder (melting point 80° C.).

Analysis: calculated: S 10.53%; found: S 10.32%.

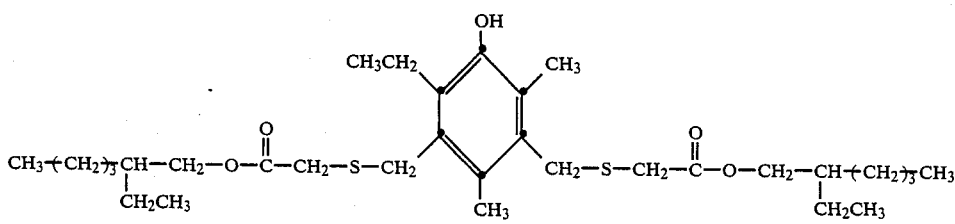

4.9 ml of tin tetrachloride are added dropwise to a mixture of 3 g of 2,4-dimethyl-6-ethylphenol, 10.6 g of 2'-ethylhexyl 2-chloromethyl-mercaptoacetate and 20 ml of CH$_2$Cl$_2$ at 0° C. under nitrogen. The reaction mixture is stirred at 50° C. for 5 hours. After cooling, the reaction mixture is poured onto water and extracted with methylene chloride.

After the solvent has been evaporated and the residue has been purified by column chromatography, 11 g of 3,5-bis-(2'-ethylhexyloxycarbonylmethyl-thiomethyl)-

USE EXAMPLES

Example A

Stabilization of polypropylene 100 parts of polypropylene powder containing 0.1% of calcium stearate are mixed with the compounds shown in the following table and the mixture is then kneaded in a Brabander Plastograph at 200° C. for 10 minutes.

The composition thus obtained is pressed to sheets 1 mm thick in a press with a surface temperature of 260° C., and strips 1 cm wide and 10 cm long are stamped out of these sheets. Several such strips from each plate are hung in a circulating air oven heated at 135° C. or 149° C. and are observed at regular intervals of time. Oxidative decomposition of these strips can be recognized by a yellow coloration starting in the form of a circle.

The period in days before decomposition is a measure of the stability of the sample.

| Compound from Example | Amount used (%) | Number of days before decomposition | |
|---|---|---|---|
| | | at 135° C. | at 148° C. |
| none | — | 1 | <1 |
| 1 + Distearyl thiodipropionate (DSTDP) | 0.1 + 0.3 | 222 | 64 |

Example B

Stabilization of styrene/butadiene copolymer

The compounds shown in the following table are dissolved in a little methanol and the solution is stirred into 100 parts of SBR latex (styrene-butadiene copolymer). A precisely defined amount of latex is then introduced into Petri dishes and dried in a drying cabinet at 80° C. Transparent films about 0.2 mm thick are obtained.

The stability of the samples after oven ageing at 135° C. is measured with the aid of the yellow coloration (Yellowness Index) at regular intervals of time. The Yellowness Index is measured in accordance with ASTM D 1925-70. The results are summarized in the following table.

| Compound from Example | Amount used (%) | Yellowness Index after the number of hours at 135° C. | | | |
|---|---|---|---|---|---|
| | | 8 | 24 | 48 | 75 |
| none | — | 37.6 | 64.4 | 89.6 | 107.4 |
| 8 | 0.25 | 12.9 | 16.7 | 19.8 | 23.7 |
| 9 | 0.25 | 12.7 | 19.5 | 20.9 | 28.7 |

Example C

Stabilization of acrylonitrile-butadiene-styrene copolymer (ABS)

0.25 g of the compounds to be tested and, if appropriate, 0.5 g of an additive are dissolved in 40 ml of a solvent mixture of hexane/isopropanol. The solution is added to a dispersion of 100 g of ABS in 600 g of water with vigorous stirring, the solution being completely absorbed by the ABS in a short time (in one minute). The ABS powder is filtered off with suction and dried at 40° C. in vacuo for 40 hours. 2% of titanium dioxide (pigment) and 1% of ethylenebis-stearic acid amide (lubricant) are added to the dry powder. The mixture is then compounded on a two-roll mill at 180° C. for 4 minutes.

A sheet 0.8 mm thick is pressed out of the rolled sheet at 175° C., and specimens with dimensions of 45×17 mm are stamped out of this. A sheet containing no compound according to the invention is produced in the same way. The effectiveness of the added compound is tested by heat ageing in a circulating air oven at 180° C. The colour development after a test period of 90 minutes serves as the criterion. The colour intensity is determined by the "Yellowness Index" in accordance with ASTM D 1925-70. Higher figures mean a more intense yellow coloration. The experiments show that the yellow coloration is effectively suppressed by the added compounds according to the invention.

| Compound from Example | Amount used (%) | Yellowness Index after 90 Minutes at 180° C. |
|---|---|---|
| none + Dilauryl thiodipropionat (DLTDP) | 0,5 | 104 |
| none + Distearyl thiodipropionat (DSTDP) | 0,5 | 104 |
| 8 + DLTDP | 0,25 + 0,5 | 36 |
| 9 + DLTDP | 0,25 + 0,5 | 51 |
| 2 + DSTDP | 0,25 + 0,5 | 31 |
| 6 + DSTDP | 0,25 + 0,5 | 31 |
| 1 + DSTDP | 0,25 + 0,5 | 41 |

Example D

Stabilization of acrylonitrile-butadiene copolymer (NBR)

Preparation of the vulcanisates: Preparation of the mixture at 50° C. on a 50×350 roll mill; friction 1:1.2; mixing time 30 minutes;

| Recipe: | |
|---|---|
| NBR (free from additives) | 100 parts |
| ZnO | 5 parts |
| Stearic acid | 0.5 part |
| Active charcoal | 75 parts |
| Dioctyl phthalate | 5 parts |
| Insoluble sulfur | 1.25 parts |
| Vulcanization accelerator (Vulk. Thiuran MS) | 0.5 part |
| Stabilizer according to the invention | 1 part |

Vulcanization of 2 mm sheets at 166° C. to T 95.

A sample without a stabilizer is produced analogously. Ageing test: 3 days "ageing" in an inert gas (argon) at 95° C. and subsequent oven ageing at 80° C.

| Compound from Example | Amount used (%) | Elongation at break (%) | | | |
|---|---|---|---|---|---|
| | | without ageing | after the number of days of oven ageing | | |
| | | | 14 | 28 | 46 |
| none | — | 410 | 190 | 100 | 40 |
| 3 | 1.0 | 430 | 250 | 210 | 150 |

What is claimed is:
1. A compound of formula I

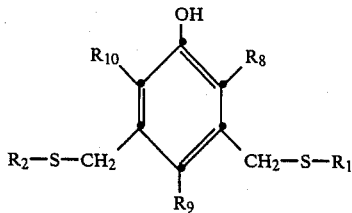

(I)

wherein $R_1$ and $R_2$ have the same meaning and are hydrogen, $C_6$-$C_{20}$alkyl with at least one tertiary C-atom, a group of the formula Ib

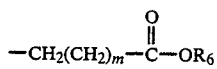

(Ib)

or a group of the formula Id

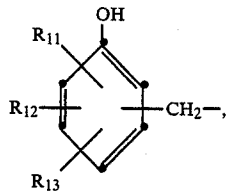

(Id)

m is zero or 1, $R_6$ is $C_6$-$C_{18}$-alkyl, $R_{11}$ is $C_1$-$C_6$-alkyl, $R_{12}$ and $R_{13}$ independently of one another are hydrogen or $C_1$-$C_6$-alkyl, and $R_8$, $R_9$ and $R_{10}$ are $C_1$-$C_4$-alkyl.

2. A compound of the formula I according to claim 1, wherein $R_{11}$ and $R_{12}$ in formula Id are $C_1$-$C_6$-alkyl.

3. A compound of the formula I according to claim 1, wherein $R_1$ and $R_2$ are $C_6$-$C_{20}$-alkyl with at least one tertiary C atom.

4. A compound of the formula I according to claim 1, wherein $R_1$ and $R_2$ are a group of the formula Ib.

5. A compound of the formula I according to claim 1, in which $R_1$ and $R_2$ are a group of the formula Id.

6. A compound of the formula I according to claim 1, wherein $R_1$ and $R_2$ are $-CH_2-COO-CH_2-CH(CH_2CH_3)-(CH_2)_3-CH_3$ and $R_8$, $R_9$ and $R_{10}$ are methyl.

7. A compound of the formula I according to claim 1, wherein $R_1$ and $R_2$ are hydrogen.

8. A compound of the formula I according to claim 6 wherein $R_1$ and $R_2$ are each a group

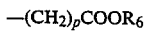

in which p is 1 or 2, and $R_6$ is $C_6$-$C_{18}$-alkyl.

9. A composition containing an organic material which is sensitive to degradation by heat or oxidation or induced by radiation and an effective stabilizing amount of at least one compound of the formula I according to claim 1.

* * * * *